United States Patent [19]

Verge et al.

[11] 4,123,529

[45] Oct. 31, 1978

[54] PHENYLPIPERAZINE DERIVATIVES

[75] Inventors: John P. Verge, Middle Assendon; William B. Jamieson, Kettlewell Close, both of England

[73] Assignee: Lilly Industries Limited, London, England

[21] Appl. No.: 813,912

[22] Filed: Jul. 8, 1977

Related U.S. Application Data

[63] Continuation-in-part of Ser. No. 781,602, Mar. 28, 1977, abandoned.

[30] Foreign Application Priority Data

Apr. 23, 1976 [GB] United Kingdom ............... 16256/76

[51] Int. Cl.² .................. A61K 31/495; C07D 413/06; C07D 417/06; C07D 407/06
[52] U.S. Cl. .................................... 424/250; 544/369; 544/379
[58] Field of Search ................. 260/268 PH; 424/250

[56] References Cited

U.S. PATENT DOCUMENTS 3,576,808  4/1971  Schut ........................... 260/268 PH
3,930,008  12/1975  Manghisi et al. ............ 260/268 PH
4,061,637  12/1977  Manghisi et al. ............ 260/268 FH

FOREIGN PATENT DOCUMENTS 781,062  5/1973  Poland.

Primary Examiner—Jose Tovar
Attorney, Agent, or Firm—James L. Rowe; Arthur R. Whale

[57] ABSTRACT

Phenylpiperazine derivatives of formula (I):

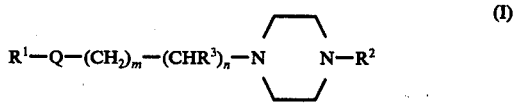

where $R^1$ is benzyl, $C_{1-6}$ alkyl or optionally substituted phenyl; $R^2$ is optionally substituted phenyl; $R^3$ is hydrogen or $C_{1-4}$ alkyl; Q is furan, thiophene, oxazole or thiazole; $m$ is 1 to 3 and $n$ is 0 or 1; and pharmaceutically-acceptable salts thereof are active in the chemotherapy of immediate hypersensitivity conditions such as asthma.

18 Claims, No Drawings

PHENYLPIPERAZINE DERIVATIVES

CROSS-REFERENCE

This application is a continuation-in-part of our co-pending application No. 781,602 filed Mar. 28, 1977, now abandoned.

This invention relates to a novel class of phenylpiperazine derivatives which possess useful pharmacological activity. Furthermore, the invention includes within its scope processes for preparing the novel compounds of the invention, pharmaceutical compositions containing the aforementioned pharmacologically active compounds as well as a method of treating animals, including humans, which comprises administering thereto a chemotherapeutically effective amount of a pharmacologically active compound or composition of the invention.

According to the present invention there is provided a phenylpiperazine derivative of formula (I):

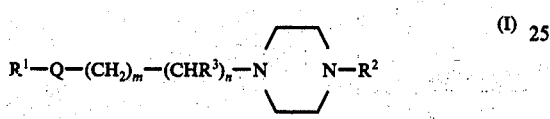

where $R^1$ is benzyl, $C_{1-6}$alkyl or phenyl optionally substituted by one or two radicals selected from halogen, $C_{1-4}$alkyl, $C_{1-4}$haloalkyl, amino, $C_{2-4}$alkanoylamino, hydroxy, $C_{1-4}$alkoxy, nitro and $C_{1-4}$alkylsulphonamido; $R^2$ is phenyl optionally substituted by one or two radicals selected from halogen, $C_{1-4}$alkyl, $C_{1-4}$haloalkyl, amino, $C_{2-4}$alkanoylamino, hydroxy, $C_{1-4}$alkoxy, nitro and $C_{1-4}$alkylsulphonamido; $R^3$ is hydrogen or $C_{1-4}$alkyl; Q is furan, thiophene, oxazole or thiazole; $m$ is 1 to 3 and $n$ is 0 or 1; or a pharmaceutically-acceptable salt thereof.

The term "$C_{1-4}$alkyl" as used herein means a straight or branched chain alkyl group containing from 1 to 4 carbon atoms e.g. methyl, ethyl, iso-propyl, n-butyl, s-butyl, iso-butyl and t-butyl. "$C_{1-4}$haloalkyl" signifies an aforementioned $C_{1-4}$alkyl group substituted by one or more fluorine, chlorine, bromine or iodine atoms, and includes groups such as trifluoromethyl or pentachloroethyl. Similarly, the term "$C_{1-4}$alkoxy" refers to the aforementioned $C_{1-4}$alkyl groups attached via an oxygen atom to the phenyl group.

Preferred classes of compounds of formula (I) are those having one or more of the following characteristics:

(a) $m$ is 1 and $n$ is 0;
(b) Q is thiazole;
(c) Q is oxazole;
(d) Q is thiophene;
(e) Q is furan;
(f) $R^1$ is $C_{1-3}$alkyl such as methyl or i-propyl;
(g) $R^1$ is phenyl;
(h) $R^1$ is benzyl;
(i) $R^2$ is phenyl substituted by one or two methyl radicals.

Particularly active classes of phenylpiperazine derivatives of formula (I) are furans of formula (II):

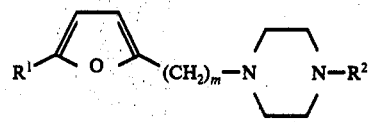

where $R^1$ is phenyl optionally substituted by one or two radicals selected from halogen, $C_{1-4}$alkyl, $C_{1-4}$alkoxy, and $C_{1-4}$haloalkyl; $R^2$ is phenyl optionally substituted by $C_{1-4}$alkyl, amino, $C_{1-4}$alkylsulphonamido and $C_{1-4}$alkoxy and $m$ is 1 or 3, with the exception of compounds in which $R^1$ is unsubstituted phenyl, $m$ is 1 and $R^2$ is unsubstituted phenyl; or where $R^1$ is methyl, $m$ is 1 and $R^2$ is phenyl optionally substituted by a single radical selected from halogen, $C_{1-4}$alkyl, $C_{1-4}$alkoxy, $C_{1-4}$haloalkyl or is disubstituted by two $C_{1-4}$alkyl radicals;

thiophenes of formula (III):

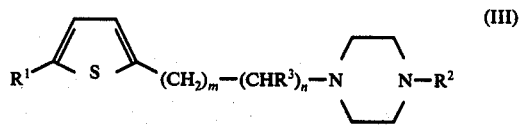

where $R^1$ is phenyl; $R^2$ is phenyl, phenyl singly substituted by $C_{1-4}$alkyl or $C_{1-4}$haloalkyl or doubly substituted by two radicals selected from the group comprising halogen, $C_{1-4}$haloalkyl and $C_{1-4}$alkyl, and where $m$ is 1 or 2 and $n = 0$; or where $m$ is 1, $n$ is 1 and $R^3$ is ethyl;

oxazoles of formula (IV):

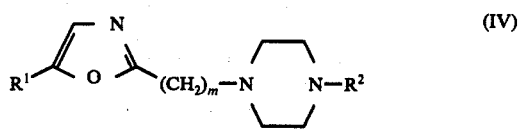

where $R^1$ is phenyl optionally substituted by $C_{1-4}$alkoxy or halogen; $R^2$ is phenyl optionally substituted by $C_{1-4}$alkyl, $C_{1-4}$haloalkyl, halogen, amino or $C_{2-4}$alkanoylamino and $m$ is 1 or 2;

thiazoles of formula (V):

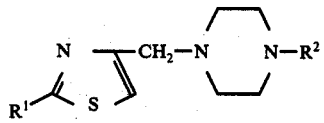

where $R^1$ is benzyl, $R^2$ is phenyl or p-halophenyl;

or thiazoles of formula:

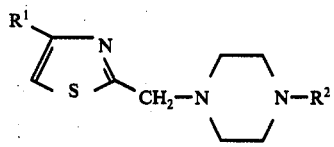

where $R^1$ is $C_{1-4}$alkyl or phenyl optionally substituted by $C_{1-4}$alkyl, $C_{1-4}$alkoxy, nitro and $C_{1-4}$haloalkyl and $R^2$ is phenyl optionally substituted by $C_{1-4}$haloalkyl;

and their pharmaceutically-acceptable salts

Preferably in the above derivatives, and where appropriate, m is 1.

Particularly preferred compounds of formula (I) are:
1-[2-(5-Phenylthiophen-2-yl)ethyl]-4-phenylpiperazine;
1-(5-Methylfuran-2-ylmethyl)-4-(3-chlorophenyl)piperazine;
1-[5-(4-Methoxyphenyl)-furan-2-ylmethyl]-4-phenylpiperazine;
1-[5-(3,4-Dimethylphenyl)-furan-2-ylmethyl]-4-phenylpiperazine;
1-{3-[5-(3,4-dichlorophenyl)-furan-2-yl]prop-1-yl}-4-(4-methylphenyl)piperazine;
1-[2-(5-Phenylthiophen-2-yl)but-1-yl]-4-phenylpiperazine;
1-(5-phenylthiophen-2-ylmethyl)-4-(3,4-dimethylphenyl)piperazine;
1-[3-(5-Phenylfuran-2-yl)prop-1-yl]-4-(4-methylphenyl)piperazine;
1-[5-(4-Methoxyphenyl)-furan-2-ylmethyl]-4-(4-methylphenyl)piperazine;
1-(5-Phenyloxazol-2-ylmethyl)-4-(4-methylphenyl)-piperazine;
1-(2-Benzylthiazol-4-ylmethyl)-4-phenylpiperazine; and their pharmaceutically acceptable acid-addition salts.

Other illustrative examples of novel compounds of the invention are:
1-(5-Phenylthiophen-2-ylmethyl)-4-(3-chlorophenyl)-piperazine;
1-(5-Phenylthiophen-2-ylmethyl)-4-(4-methoxyphenyl)-piperazine;
1-[5-(3-Trifluoromethyl-4-chlorophenyl)-furan-2-ylmethyl]-4-(4-fluorophenyl)piperazine;
1-[3-(5-Phenylfuran-2-yl)prop-1-yl]-4-(3-trifluoromethylphenyl)piperazine;
1-(2-Methylthiazol-4-ylmethyl)-4-(3-chlorophenyl)piperazine;
1-[2-(4-Phenylthiazol-2-yl)ethyl]-4-(4-aminophenyl)piperazine;
1-[2-(4-Phenylthiazol-2-yl)ethyl]-4-(4-nitrophenyl)piperazine;
1-(5-Phenyloxazol-2-ylmethyl)-4-phenylpiperazine;
1-[4-(3-Trifluoromethylphenyl)-thiazol-2-ylmethyl]-4-phenylpiperazine;
1-(4-Phenylthiazol-2-ylmethyl)-4-phenylpiperazine;
1-{2-[5-(4-Chlorophenyl)oxazol-2-yl]-ethyl}-4-phenylpiperazine;
1-[2-(5-Phenyloxazol-2-yl)ethyl]-4-(4-chlorophenyl)-piperazine;
1-[2-(5-Phenyloxazol-2-yl)ethyl]-4-(4-methoxyphenyl)-piperazine;
1-[1-(5-Phenyloxazol-2-yl)prop-2-yl]-4-(4-methylphenyl)-piperazine;
1-[1-(5-Phenyloxazol-2-yl)ethyl]-4-(4-methylphenyl)-piperazine;
1-(5-Phenyloxazol-2-ylmethyl)-3-methyl-4-(4-methylphenyl)-piperazine;
1-(5-Phenyloxazol-2-ylmethyl)-2,3-dimethyl-4-(4-methylphenyl)-piperazine;
1-{2-[4-(Chlorophenyl)-thiazol-2-yl]ethyl}-4-phenylpiperazine;
1-[2-(4-Phenylthiazol-2-yl)ethyl]-4-(4-chlorophenyl)-piperazine;
1-[2-(4-Phenylthiazol-2-yl)ethyl]-4-(4-methoxyphenyl)-piperazine;
1-[1-(4-Phenylthiazol-2-yl)prop-2-yl]-4-(4-methyl-phenyl)-piperazine;
1-[1-(4-Phenylthiazol-2-yl)ethyl]-4-(4-methylphenyl)-piperazine;
1-(4-Phenylthiazol-2-ylmethyl)-4-(4-methanesulphonamidophenyl)-piperazine;
1-{2-[5-(4-Chlorophenyl)-furan-2-yl]ethyl}-4-phenylpiperazine;
1-[2-(5-Phenylfuran-2-yl)ethyl]-4-(4-chlorophenyl)-piperazine;
1-[2-(5-Phenylfuran-2-yl)ethyl]-4-(4-methoxyphenyl)-piperazine;
1-[1-(5-Phenylfuran-2-yl)prop-2-yl]-4-(4-methylphenyl)-piperazine;
1-[1-(5-Phenylfuran-2-yl)ethyl]-4-(4-methylphenyl)-piperazine;
1-(5-Phenylfuran-2-ylmethyl)-4-(4-methylphenyl)-piperazine;
1-(5-Phenylfuran-2-ylmethyl)-4-(4-methanesulphonamidophenyl)-piperazine;
1-[4-(4-Phenylthiazol-2-yl)but-1-yl]-4-phenylpiperazine;
1-(5-Phenylthiophen-2-ylmethyl)-4-(4-methylphenyl)-piperazine;
1-(5-Phenylthiophen-2-ylmethyl)-4-phenylpiperazine;
1-(5-Methyloxazol-2-ylmethyl)-4-phenylpiperazine;
1-(4-Methyloxazol-2-ylmethyl)-4-(4-methylphenyl)-piperazine;
1-[2-(5-Methyloxazol-2-yl)ethyl]-4-(4-chlorophenyl)-piperazine;
1-[2-(4-Methyloxazol-2-yl)ethyl]-4-(3-methylphenyl)-piperazine;
1-[3-(5-Methyloxazol-2-yl]-4-(2-chlorophenyl)piperazine;
1-(5-Benzyloxazol-2-ylmethyl)-4-(4-nitrophenyl)piperazine;
1-(4-Benzyloxazol-2-ylmethyl)-4-(3-acetylaminophenyl)piperazine;
1-[2-(5-Benzyloxazol-2-yl)ethyl]-4-(4-nitrophenyl)piperazine;
1-[2-(5-Benzyloxazol-2-yl)ethyl]-4-(4-ethylphenyl)piperazine;
1-[3-(5-Benzyloxazol-2-yl)prop-1-yl]-4-(4-ethoxyphenyl)piperazine;
1-(5-Methylthiazol-2-ylmethyl)-4-phenylpiperazine;
1-(4-Methylthiazol-2-ylmethyl)-4-(4-methylphenyl)piperazine;
1-[2-(5-Methylthiazol-2-yl)ethyl]-4-(4-chlorophenyl)-piperazine;
1-[2-(4-Methylthiazol-2-yl)ethyl]-4-(3-methylphenyl)-piperazine;
1-[3-(5-Methylthiazol-2-yl)prop-1-yl]-4-(2-chlorophenyl)piperazine;
1-(5-Benzylthiazol-2-ylmethyl)-4-(4-nitrophenyl)-piperazine;
1-(4-Benzylthiazol-2-ylmethyl)-4-(3-acetylaminophenyl)piperazine;
1-[2-(5-Benzylthiazol-2-yl)ethyl]-4-(4-aminophenyl)piperazine;
1-[2-(5-Benzylthiazol-2-yl)ethyl]-4-(4-ethylphenyl)piperazine;
1-[3-(5-Benzylthiazol-2-yl)prop-1-yl]-4-(4-ethoxyphenyl)piperazine;
1-(5-Methylfuran-2-ylmethyl)-4-phenylpiperazine;
1-(4-Methylfuran-2-ylmethyl)-4-(4-methylphenyl)piperazine;
1-[2-(5-Methylfuran-2-yl)ethyl]-4-(4-chlorophenyl)-piperazine;
1-[2-(4-Methylfuran-2-yl)ethyl]-4-(3-methylphenyl)-piperazine;
1-[3-(5-Methylfuran-2-yl)prop-1-yl]-4-(2-chlorophenyl)piperazine;

1-(5-Benzylfuran-2-ylmethyl)-4-(4-nitrophenyl)piperazine;

1-(4-Benzylfuran-2-ylmethyl)-4-(3-acetylaminophenyl)-piperazine;

1-[2-(5-Benzylfuran-2-yl)ethyl]-4-(4-ethylphenyl)piperazine;

1-[3-(5-Benzylfuran-2-yl)prop-1-yl]-4-(4-ethoxyphenyl)-piperazine;

1-(5-Methylthiphen-2-ylmethyl)-4-phenylpiperazine;

1-(4-Methylthiophen-2-ylmethyl)-4-(4-methylphenyl)-piperazine;

1-[2-(5-Methylthiophen-2-yl)ethyl]-4-(4-chlorophenyl)-piperazine;

1-[2-(4-Methylthiophen-2-yl)ethyl]-4-(3-methylphenyl)-piperazine;

1-[3-(5-Methylthiophen-2-yl)prop-1-yl]-4-(2-chlorophenyl)piperazine;

1-(5-Benzylthiophen-2-ylmethyl)-4-(4-nitrophenyl)piperazine;

1-(4-Benzylthiophen-2-ylmethyl)-4-(3-acetylaminophenyl)piperazine;

1-[2-(5-Benzylthiophen-2-yl)ethyl]-4-(4-nitrophenyl)-piperazine;

1-[2-(5-Benzylthiophen-2-yl)ethyl]-4-(4-ethylphenyl)-piperazine;

1-[3-(5-Benzylthiophen-2-yl)prop-1-yl]-4-(4-ethoxyphenyl)piperazine;

and their pharmaceutically-acceptable acid-addition salts.

According to a further aspect of the present invention there is provided a method of preparing a piperazine derivative of formula (I), or an acid-addition salt thereof, which comprises:

(A) condensing a compound of formula (VI):

$$R^1-Q-(CH_2)_m-(CHR^3)_n-L \quad (VI)$$

where L represents a leaving group, with a compound of formula (VII):

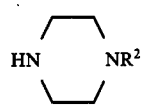

(VII)

(B) reducing a compound of formula:

(VIII)

(i) $R^1-Q-(CH_2)_{m-1}-\overset{\overset{O}{\|}}{C}-N\underset{\underset{\diagdown\_\_\diagup}{}}{\overset{\diagup\mbox{---}\diagdown}{}}N-R^2$ to form a compound in which n is 0; or

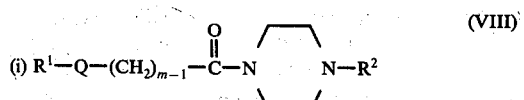

(IX)

(ii) $R^1-Q-(CH_2)_m-CR^3\overset{(+)}{=}N\underset{\underset{\diagdown\_\_\diagup}{}}{\overset{\diagup\mbox{---}\diagdown}{}}N-R^2$ to form a compound in which n is 1; or (C) cyclising a compound of formula (X):

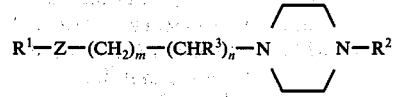

(X)

where Z is a group cyclisable to Q to form a compound of formula (I) in which Q is oxazole.

The above condensation (A) is preferably carried out in the presence of a proton acceptor such as a base, for example, sodium carbonate. Polar solvents such as alkanols, e.g. ethanol, are suitable solvents for the reaction which is advantageously accomplished by heating under reflux. The leaving group L may be any radical known to be effective in such condensation reactions but it should be mentioned that halogen atoms, for instance chlorine, or methylsulphonyl or substituted benzene sulphonyl groups give good results in this reaction. This reaction is preferably effected in the temperature range from 20° to 150° C. Compounds of formula (VI) are either known (see J.A.C.S. 56 470–1(1934) and 53 1470–3(1931)) or can be prepared by known techniques.

Reduction of the amide of formula (VIII) can be effected using chemical reducing agents such as $B_2H_6$ or lithium aluminium hydride. Ethereal solvents such as tetrahydrofuran are of value in effecting the reaction which is preferably carried out at a temperature range from 0° to 80° C. The amides of formula (VIII) can be prepared by reaction of an acid chloride (prepared for instance from the corresponding acid by reaction with thionyl chloride) of formula:

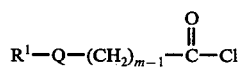

with the phenylpiperazine of formula:

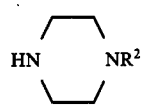

The reduction of compounds of formula (IX) can be carried out using the reaction conditions described in J.A.C.S. 93 2897–2904 (1971) or in Synthesis 135–146 (1975). The reduction is preferably accomplished using sodium cyanoborohydride but other forms of reduction, for example, using catalytic hydrogenation or other suitable chemical reducing agents are possible. As before, the reduction is preferably accomplished in the temperature range of from 0° to 80° C.

Compounds of formula (X) are normally prepared by reaction of the corresponding carbonyl compound of formula:

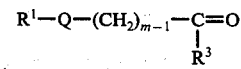

with the appropriate phenyl base of formula

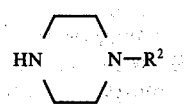

in the presence of a proton donor, such as acetic acid.

The nature of Z in the above cyclisation reaction (C) and the reaction conditions necessary to effect the desired ring-closure will be well-known to those skilled in the art. In case of doubt recourse may be had to standard treatises in the art such as *Chemical Reviews*, 75, 389–437 (1975) and *Advances in Heterocyclic Chemistry* 17 (1974).

Preferably, Z is a group of formula:

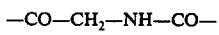

Thus, compounds of formula (XI)

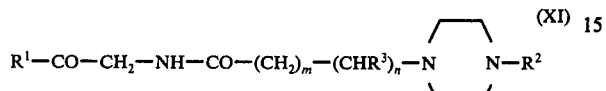

can be cyclised to compounds of formula:

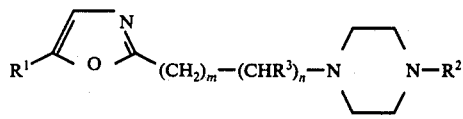

using dehydrating agents such as polyphosphoric acid, phosphorous oxychloride or concentrated sulphuric acid. The reaction is preferably accomplished at a temperature range of from 80° to 180° C.

Compounds of formula (XI) may be prepared by reacting the corresponding bromo derivative of formula:

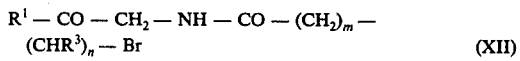

with the corresponding base of formula

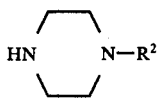

in the presence of an acid scavenger such as sodium carbonate.

The compounds of formula (XII) may themselves be prepared by reaction of the amine of formula:

with the corresponding acid chloride of formula

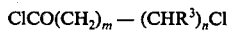

using dimethylformamide as solvent.

The compounds of formula (I) produced by the foregoing processes may be isolated per se or in acid-addition salt form.

The acid-addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic maleic, hydroxymaleic, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid-addition salts, other salts are also included within the scope of acid-addition salts such as, for example, those with picric or oxalic acid; they may serve as intermediates in the purification of the compounds or in the preparation of other, for example, pharmaceutically acceptable, acid-addition salts, or are useful for identification, characterisation or purification of the bases.

A resulting acid-addition salt may be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate; with ammonia; or with a hydroxyl ion exchange preparation, or with any other suitable reagent.

A resulting acid-addition salt may also be converted into another acid-addition salt according to known methods; for example, a salt with an inorganic acid may be treated with a metal salt, for example, a sodium, barium or silver salt, of an acid in a suitable diluent, in which a resulting inorganic salt is insoluble and is thus removed from the reaction medium. An acid addition salt may also be converted into another acid-addition salt by treatment with an anion exchange preparation.

According to a further aspect of the invention there is provided a pharmaceutical formulation which comprises a compound of formula (I), or a pharmaceutically-acceptable salt thereof, associated with a pharmaceutically-acceptable carrier therefor.

Compounds of formula (I) and their pharmaceutically-acceptable salts have been shown to be useful in the prophylactic treatment of immediate hypersensitivity diseases in mammals including asthma in humans.

This activity has been demonstrated in guinea pigs using the well-known "Herxheimer" test described for instance in the *Journal of Physiology* (*London*) 117, 251 (1952). The test is based on an allergic bronchospasm induced in guinea pigs which closely resembles an asthmatic attack in man. The mediators causing the bronchospasm are very similar to those released when sensitised human lung tissue is challenged with an antigen. Although the antibody involved is $I_gG_1$ in the guinea pig and $I_gE$ in man, both antibodies are homocytotrophic and bind strongly to tissue. Compounds of the invention have exhibited activity in the "Herxheimer" test at dosages ranging from 25 mg/kg to 200 mg/kg.

The compounds or compositions of the present invention may be administered by various routes and for this purpose may be formulated in a variety of forms. Thus the compounds or compositions may be administered orally, rectally, topically or parenterally (e.g. by injection or by continuous or discontinuous intravenous infusion) in the form of, for example, tablets, lozenges, sub-lingual tablets, sachets, cachets, elixirs, suspensions, suppositories, aerosols, ointments (for example, containing from 1 to 10% by weight of the active compound in a suitable base) soft and hard gelatin capsules, injection solutions and suspensions in physiologically acceptable media, and sterile packaged powders adsorbed onto a support material for making injection solutions.

Advantageously for this purpose, compositions may be provided in dosage unit form, preferably each dosage unit containing from 50 to 500 mg. (from 5.0 to 50 mg. in the case of parenteral administration, from 5.0 to 50 mg. in the case of inhalation and from 25 to 500 mg. in the case of oral or rectal administration) of a compound of formula I. Dosages of from 2 to 50 mg/kg per day, of active ingredient may be administered in allergic diseases of humans although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consists of at least one compound of formula I mixed with a carrier, or diluted by a carrier, or enclosed or encapsulated by an ingestible carrier in the form of a capsule, sachet, cashet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The following Examples illustrate the invention.

EXAMPLE 1

(a) 2-Acetoxythioacetamide

A stream of dry $H_2S$ gas was passed rapidly into a solution of 2-acetoxyacetonitrile (150 g; 1.52 mole) and triethanolamine (20 ml) in dry ethanol (500 ml) with vigorous stirring. The internal temperature rose to ca. 55° C. The gas flow was maintained for 3 hours whereupon G.L.C. indicated that the reaction was complete. Excess $H_2S$ gas was blown off with a stream of nitrogen and solvent EtOH evaporated to dryness. The remaining sticky crystalline mass was extracted with boiling ether, a small insoluble residue being discarded. The combined extracts were treated with decolourising charcoal, filtered and evaporated to approximately 400 ml volume. On cooling to 0° C. there was obtained some 170 g. of somewhat sticky 2-acetoxythiocetamide. This was used for the next stage without further characterisation.

(b) 2-Hydroxymethyl-4-phenylthiazole

2-Bromoacetophenone (39.9 g; 0.2 mole) and 2-acetoxythioacetamide (30 g; 0.225 mole) were dissolved in dioxan (150 ml). The mixture was stirred and heated on a steam bath for 15 minutes, yielding a mass of crystals. Aqueous 5N HCl (40 ml) was added and the heating continued for a further 30 minutes. The dioxan was evaporated under vacuum and the residue neutralised with aqueous $Na_2CO_3$ solution. The solid was collected, washed with water and dried. After recrystallisation from benzene the product weighed 33.5 g (87%) and had a m.p. of 88°–9° C.

(c) 2-Chloromethyl-4-phenylthiazole.

Thionyl chloride (6.25 g, 0.052 mole) was added dropwise to a stirred solution of 2-hydroxymethyl-4-phenylthiazole (9.55 g; 0.05 mole) and dry pyridine (4.0 g; 0.051 mole) in dry benzene (60 ml) held at room temperature. The mixture was stirred and heated to boiling for 1 hour. The cooled reaction mixture was then shaken with 2 × 70 ml $H_2O$ and dried over anhydrous $MgSO_4$. The solvent was removed under vacuum and the remaining red oil extracted with 40°–60° C. petroleum ether (100 ml), discarding a small tarry residue. The extract was treated with decolourising charcoal, filtered and evaporated, leaving a yellow-red oil that crystallised on refrigeration.

Yield 9.9 g 94.5%

No further purification was undertaken, and the material was used directly for the next stage.

(d) 1-(4-Phenyl-2-thiazolylmethyl)-4-phenylpiperazine

A mixture of crude 2-chloromethyl-4-phenylthiazole (4.19g; 0.02 mole), N-phenylpiperazine (3.24 g; 0.02 mole) and finely-powdered, anhydrous sodium carbonate in absolute ethanol (60 ml) was stirred and boiled under reflux for 8 hours. The solvent was evaporated to dryness, solid residue suspended in water (100 ml) and then extracted with 2 × 100 ml $CH_2Cl_2$. The extracts were washed with water and dried over anhydrous $MgSO_4$. On evaporation of the solvent, and recrystallisation of the residue from benzene/60°–80° C. petroleum ether mixture (with charcoal treatment) there was obtained the required product (5.03 g; 75%) having m.p. 142°–3° C.

EXAMPLES 2 to 19

Similarly, there were prepared:

(2) 1-(4-Phenyl-2-thiazolylmethyl)-4-(3-bromophenyl)-piperazine, m.p. 127.5°–128.5° C.

(3) 1-(4-Phenyl-2-thiazolylmethyl)-4-(3,4-dichlorophenyl)-piperazine, m.p. 144°–6° C.

(4) 1-(4-Phenyl-2-thiazolylmethyl)-4-(3-trifluoromethylphenyl)-piperazine, m.p. 112°–3° C.

(5) 1-(4-Phenyl-2-thiazolylmethyl)-4-(4-chloro-3-trifluoromethylphenyl)-piperazine, m.p. 117°–9° C.

(6) 1-(4-Phenyl-2-thiazolylmethyl)-4-(4-methylphenyl)-piperazine, m.p. 141°–3° C.

(7) 1-(4-Phenyl-2-thiazolylmethyl)-4-(4-methoxyphenyl)-piperazine, m.p. 148°–9° C.

(8) 1-[4-(4-Chlorophenyl)-2-thiazolylmethyl]-4-phenyl-piperazine, m.p. 164°–5° C.

(9) 1-[4-(4-Chlorophenyl)-2-thiazolylmethyl]-4-(3-bromophenyl)-piperazine, m.p. 100°–101° C.

(10) 1-[4-(4-Bromophenyl)-2-thiazolylmethyl]-4-phenylpiperazine, m.p. 166° C.

(11) 1-[4-(3-Chlorophenyl)-2-thiazolylmethyl]-4-phenylpiperazine, m.p. 129°–131° C.

(12) 1-[4-(2-Chlorophenyl)-2-thiazolylmethyl]-4-phenylpiperazine, m.p. 100°–101° C.
(13) 1-[4-(3,4-Dichlorophenyl)-2-thiazolylmethyl]-4-phenylpiperazine, m.p. 138°–139.5° C.
(14) 1-[4-(3-Trifluoromethylphenyl)-2-thiazolylmethyl]-4-phenylpiperazine m.p. 110°–111° C.
(15) 1-[4-(4-Methoxyphenyl)-2-thiazolylmethyl]-4-phenylpiperazine. HCl m.p. 201° C.
(16) 1-[4-(4-Methylphenyl)-2-thiazolylmethyl]-4-phenylpiperazine. HCl m.p. 175°–180° C.
(17) 1-[4-(3-Methylphenyl)-2-thiazolylmethyl]-4-phenylpiperazine, m.p. 113°–113.5° C.
(18) 1-[4-(4-Hydroxyphenyl)-2-thiazolylmethyl]-4-phenylpiperazine, m.p. 228°–230° C.
(19) 1-[4-(4-Nitrophenyl)-2-thiazolylmethyl]-4-phenylpiperazine, m.p. 195°–8° C.

EXAMPLE 20

(a) N-Phenacyl chloroacetamide

Chloroacetyl chloride (25 g; 0.226 mole) was added slowly to a stirred solution of phenacylamine hydrochloride (25.9 g; 0.151 mole) in anhydrous dimethylformamide (DMF) (80 ml) at room temperature. The internal temperature rose to ca. 40° C. The mixture was stirred for 4 hours after the addition and the bulk of the DMF evaporated under vacuum. The residue was treated with water (200 ml) and the crystalline precipitate collected, washed with water and dried. Yield 24.75 g (77%). m.p. 118°–119° C.

(b) 2-Chloromethyl-5-phenyloxazole

N-Phenacyl chloroacetamide (22.6 g; 0.107 mole) was mixed with polyphosphoric acid (200 g) and the mass heated with stirring for 30 minutes at 150° C. The hot liquid was then poured with vigorous stirring into water (800 ml). The mixture so formed was extracted with 3 × 100 ml chloroform, the extracts washed by shaking with water and dried over magnesium sulphate. The CHCl₃ was evaporated off and the remaining oil extracted with 400 ml boiling 60°–80°0 C. petroleum ether. The resultant solution was treated with decolourising charcoal to remove tarry matter and evaporated, giving a pale yellow oil which crystallized rapidly. Yield 18.8 g (91%) m.p. 70°–1° C.

(c) 1-(5-Phenyl-oxazol-2-ylmethyl)-4-phenylpiperazine

A solution of 2-choromethyl-5-phenyloxazole (3.87 g; 0.02 mole) and N-phenylpiperazine (3.25 g; 0.02 mole) in absolute ethanol (60 ml) was boiled and stirred with finely powdered anhydrous sodium carbonate (5 g) for 6 hours.

The solution was evaporated to dryness and treated with water (60 ml). The suspension thus obtained was extracted with 2 × 70 ml. dichloromethane. The extracts were dried over magnesium sulphate and evaporated to dryness. The solid residue was recrystallised from 80°–100° C. petroleum ether with the use of decolourising charcoal.

Yield 4.67 g. m.p. 96° C.

EXAMPLES 21–35

Similarly, there were prepared:
(21) 1-(5-Phenyl-oxazol-2-ylmethyl)-4-(4-methylphenyl)-piperazine, m.p. 113°–114° C.
(22) 1-(5-Phenyl-oxazol-2-ylmethyl)-4-(3-chlorophenyl)-piperazine, m.p. 73° C.
(23) 1-(5-Phenyl-oxazol-2-ylmethyl)-4-(4-chlorophenyl)-piperazine, m.p. 125°–6° C.
(24) 1-(5-Phenyl-oxazol-2-ylmethyl)-4-(3-trifluoromethylphenyl)-piperazine, m.p. 69°–70° C.
(25) 1-(5-Phenyl-oxazol-2-ylmethyl)-4-(3,4-dichlorophenyl)-piperazine, m.p. 134°–5° C.
(26) 1-(5-Phenyl-oxazol-2-ylmethyl)-4-(4-methoxyphenyl)-piperazine, m.p. 121°–2° C.
(27) 1-(5-Phenyl-oxazol-2-ylmethyl)-4-(3-methoxyphenyl)-piperazine, m.p. 100° C.
(28) 1-(5-Phenyl-oxazol-2-ylmethyl)-4-(2,4-dimethoxyphenyl)-piperazine m.p. 89°–91° C.
(29) 1-(5-Phenyl-oxazol-2-ylmethyl)-4-(3,4-dimethoxyphenyl)-piperazine, m.p. 93°–5° C.
(30) 1-(5-Phenyl-oxazol-2-ylmethyl)-4-(4ethoxyphenyl)-piperazine, m.p. 98° C.
(31) 1-[5-(4-Fluorophenyl)-oxazol-2-ylmethyl]-4-phenylpiperazine, m.p. 114°–116° C.
(32) 1-[5-(4-Fluorophenyl)-oxazol-2-ylmethyl]-4-(4-methoxyphenyl)-piperazine, m.p. 112° C.
(33) 1-[5-(4-Methoxyphenyl)-oxazol-2-ylmethyl]-4-phenylpiperazine, m.p. 112°–115° C. (34) 1-[5-(4-Methoxyphenyl)-oxazol-2-ylmethyl]-4-(4-methoxyphenyl)-piperazine, m.p. 148°–50° C.
(35) 1-(5-Phenyloxazol-2-ylmethyl)-4-(4-nitrophenyl)-piperazine, m.p. 170°–2° C.

EXAMPLE 36

1-(5-Phenyloxazol-2-ylmethyl)-4-(4-aminophenyl)-piperazine

A solution of 1-(5-phenyloxazol-2-ylmethyl)-4-(4-nitrophenyl)-piperazine (7.28 g; 0.02 mole) in glacial acetic acid (50 ml) was hydrogenated over 5% Palladium-on-charcoal catalyst (100 mg) at atmospheric pressure and room temperature, until the uptake of hydrogen was complete. The solvent was evaporated off under vacuum and the residue treated with aqueous sodium bicarbonate solution, yielding a white crystalline solid. Weight after drying = 6.54 g (98%), m.p. 130° C.

EXAMPLE 37

1-(5-Phenyloxazol-2-ylmethyl)-4-(4-acetamidophenyl)-piperazine

The 4-aminophenyl compound of Example 36 (3.0 g; 0.009 mole) was warmed on a steam bath with glacial acetic acid (5 ml) and acetic anhydride (10 ml) for 1 hour. The mixture was poured into water (200 ml), stirred well and the collected precipitate washed with water and dried. After recrystallisation from methanol the product weighed 2.45 g and melted at 196°–7° C.

EXAMPLE 38

1-(5-Phenyloxazol-2-ylmethyl)-4-(4-hydroxyphenyl)-piperazine

Propane-1-thiol (5.02 g; 0.066 mole) as added slowly to a stirred suspension of 50% sodium hydride/mineral oil mixture (3.17 g; 0.066 mole) in anhydrous dimethylformamide (140 ml). To the solution of sodium propan-1-thiolate thus formed was added 1-(5-phenoloxazol-2-ylmethyl)-4-(4-methoxyphenyl)-piperazine (7.7 g; 0.022 mole). The solution was heated to reflux on an oil bath for 10 hours under an atmosphere of nitrogen. The mixture was then poured into water (600 ml) and extracted with 3 × 200 ml ethyl acetate. The extracts were shaken several time with water, dried and evaporated to a white solid. After recrystallisation from dioxan/ 60°-80° C. petroleum ether, the product weighed 5.5 g (74.5%), m.p. 189°-190° C.

EXAMPLE 39

1-[2-(5-Phenyloxazol-2-yl)-ethyl]-4-phenylpiperazine (a) N-Phenacyl-3-bromopropanamide 3-Bromopropionyl chloride (25 g; 0.146 mole) was added slowly to a stirred suspension of phenacylamine hydrochloride (17.15 g; 0.1 mole) in dry dimethylformamide (50 ml) at room temperature. The internal temperature rose to ca. 40° C. The mixture was stirred for 2 hours and the DMF removed under vacuum. The residue was diluted with water (200 ml) and the crystalline solid collected, washed with water and dried. Weight of product = 9.49 g (35%), m.p. 114° C.

(b) N-Phenacyl-3-(4-phenylpiperazin-1-yl)-propanamide

A solution of N-phenacyl-3-bromopropanamide (10.2 g; 0.038 mole) and N-phenylpiperazine (12.0 g; 0.074 mole) in dry DMF (100 ml) was stirred with anhydrous, finely-powdered sodium carbonate (15.0 g) for 18 hours at room temperature. The temperature was then increased to 80° C. and held for 12 hours to complete the reaction. The DMF was evaporated off under vacuum and the residue diluted with water (100 ml). The mixture was extracted with chloroform (3 × 100 ml). The extracts were shaken with 2 × 100 ml 2N HCl and the organic layer discarded. The aqueous layer was basified with NaOH solution to pH 9 and extracted with 3 × 75 ml CHCl₃. The extracts were washed with water and dried. After removal of the solvent the remaining viscous gum triturated with ether to give a buff-coloured solid. After recrystallisation from isopropanol the product weighed 6.0 g and melted at 126° C.

(c) 1-[2-(5-Phenyloxazol-2-yl)-ethyl]-4-phenylpiperazine

N-Phenacyl-3-(4-phenylpiperazine-1-yl)-propanamide (4.03 g; 0.011 mole) was mixed with polyphosphoric acid (36 g) and stirred and heated at 140° C. for 30 minutes. The mixture was dissolved in water (100 ml), cooled, and extracted (2 × 30 ml chloroform). The extracts were discarded and the aqueous phase basified to pH 9 with 50% aqueous NaOH solution. The emulsion formed was extracted with 3 × 100 ml chloroform, the extracts dried and evaporated. The crystalline residue was recrystallised from 60°-80° C. petroleum ether. Yield 2.6 g m.p. 84°-5° C.

EXAMPLE 40

1-[5-(3-Trifluoromethylphenyl)-furan-2-ylmethyl]-4-phenylpiperazine (a) 2-Hydroxymethyl-5-(3-trifluoromethylphenyl)-furan 2-(3-Trifluoromethylphenyl)-furan (*J. Chem. Soc.* (C) 1968, 2737 and *Acta Chem Scand.* 24, 2379 (1970))(21.2 g; 0.1 mole) was stirred in tetrahydrofuran (100 ml), cooled to −40° C. and n-butyl lithium (0.1 mole, solution in hexane) was added dropwise. After stirring for 1 hour at −40° C., paraformaldehyde (3.3 g; 0.11 mole) was added gradually. The mixture was stirred at −40° C. for 30 minutes, then the temperature was allowed to rise. At 10° C. an exothermic reaction set in and the temperature gradually rose to 40° C. (over 10 minutes), then gradually fell back to 20° C. After stirring for further 1 hour the clear brown solution was poured onto ice/water, adjusted to pH ca 4 with dilute hydrochloric acid and extracted via ethyl acetate. The dried acetate extract (MgSO₄) was evaporated to give a brownish yellow viscous oil which was distilled in vacuo to give 2-hydroxymethyl-5-(3-trifluoromethylphenyl)-furan as a colourless liquid b.p. 125° C./0.5 mm., (16.2 g), which on standing gave crystals, m.p. 45° C.

(b) 2-Bromomethyl-5-(3-trifluoromethylphenyl)-furan

The hydroxymethyl compound (4.84 g; 0.02 mole) prepared in (a) above, was dissolved in dimethylformamide (30 ml) cooled to 0°-5° C. and thionyl bromide (1.7 ml; 0.02 mole) was added dropwise with stirring. After 2 hours the greenish-yellow solution was poured onto ice/water and extracted via diethyl ether. The ether extract was washed with NaCl (saturated solution) dried over molecular sieve 3A and evaporated to give a light brown oil which slowly crystallised (4.6 g).

(c) 1-[5-(3-Trifluoromethylphenyl)-furan-2-ylmethyl]-4-phenylpiperazine

The bromomethyl product (0.015 mole) of (b) above was stirred in dioxan (50 ml) with N-phenylpiperazine (2.75 g; 0.017 mole) in the presence of anhydrous sodium carbonate (1.5 g) and the mixture heated under reflux for 7 hours, poured onto ice/water and extracted via chloroform. The chloroform extract was washed with water, then with saturated salt solution and finally evaporated to give an oil which on treatment with ethereal hydrochloric acid gave a cream coloured crystalline solid (2.1 g). This hydrochloride (2 g) was dissolved in chloroform (15 ml), stirred with water (15 ml) and a saturated solution of sodium carbonate added dropwise until alkaline. The phases were separated and the chloroform layer was evaporated to give a strawcoloured oil (1.7 g) which slowly crystallised and was recrystallised from petroleum ether 60/80° C. to give the title compound 1-[5-(3-trifluoromethylphenyl)-furan-2-ylmethyl]-4-phenylpiperazine, 1.2 g, m.p. 94° C.

In a similar manner were prepared the following except that the intermediate hydroxymethyl compounds were converted to the chloromethyl compounds via thionyl chloride.

EXAMPLE 41

1-[5-(4-Chlorophenyl)-furan-2-ylmethyl]-4-phenylpiperazine m.p. 140° C.

EXAMPLE 42

1-[5-(4-Chlorophenyl)-furan-2-ylmethyl]-4-(3-trifluoromethylphenyl)-piperazine monohydrochloride The free base was obtained as an intractable viscous oil and was converted to the monohydrochloride, m.p. 220° C.

EXAMPLE 43

1-[5-(4-Chlorophenyl-furan-2-ylmethyl]-4-(3-chlorophenyl)-piperazine monohydrochloride m.p. 215° C.

EXAMPLE 44

1-[5-(4-Chlorophenyl)-furan-2-ylmethyl]-4-(3-bromophenyl)-piperazine monohydrochloride 5-(4-Chlorophenyl)-2-furoic acid (*Australian Journal of Chemistry*, 26, 1147 (1973))(6.67 g; 0.03 mole) was refluxed in benzene (100 ml) with thionyl chloride (4.5 ml) for 1.5 hours. After removal of the excess thionyl chloride, the remaining acid chloride in benzene was added dropwise with stirring and cooling to a mixture of N-(3-bromophenyl)-piperazine (7.23 g; 0.03 mole) and triethylamine (4.5 ml, ca. 0.03 mole) in benzene (100 ml). After stirring for 1 hour at room temperature, the mixture was shaken with water (100 ml). The separated benzene phase was further washed with saturated salt solution, then evaporated to give an oil which readily crystallised. The product was recrystallised from ethyl acetate/60°–80° C. petroleum ether (1/3 $v/v$) to yield 1-[5-(4-chlorophenyl)-2-furoyl]-4-(3-bromophenyl)-piperazine (12.3 g) m.p. 130° C.

The above tertiary amide (4.45 g; 0.01 mole) was dissolved in dry tetrahydrofuran (30 ml) and added dropwise with stirring and cooling to 0° C. to a solution of diborane in tetrahydrofuran (20 ml, 1M solution) (N.B. the reaction was carried out under nitrogen). The temperature rose to ca. 8° C. and the resultant hazy solution was refluxed for 1 hour. The clear pale yellow solution was cooled, then heated on a steam bath for 15 minutes with 5N HCl (20 ml). After again cooling the solution was made alkaline (4N NaOH) and extracted via diethyl ether. The ether extract after drying over MgSO₄ was evaporated to give an oil which was converted to its monohydrochloride to give the title compound. (2.8 g) m.p. 217° C.

In a similar manner were prepared the following:

EXAMPLE 45

1-[5-(4-Chlorophenyl)-furan-2-ylmethyl]-4-(3-trifluoromethyl-4-chlorophenyl)piperazine m.p. 104° C.

EXAMPLE 46

1-[2-(4-Methylphenyl)-furan-2-ylmethyl]-4-phenylpiperazine m.p. 87° C.

EXAMPLE 47

1-[5-(2-Methylphenyl)-furan-2-ylmethyl]-4-phenylpiperazine m.p. 67° C.

EXAMPLE 48

1-[5-(3,4-Dichlorophenyl)-furan-2-ylmethyl]-4-phenylpiperazine m.p. 92° C.

EXAMPLE 49

1-[5-(3-Trifluoromethyl-4-chlorophenyl)-furan-2-ylmethyl]-4-phenylpiperazine m.p. 102° C.

EXAMPLE 50

1-[5-(3-Trifluoromethyl-4-chlorophenyl)-furan-2-ylmethyl]-4-(3-chlorophenyl)piperazine monohydrochloride m.p. 216° C.

EXAMPLE 51

1-[5-(3-Trifluoromethyl-4-chlorophenyl)-furan-2-ylmethyl]-4-(4-methylphenyl)piperazine m.p. 126° C.

EXAMPLE 52

1-(5-Phenylfuran-2-ylmethyl)-4-(3-chlorophenyl)-piperazine monohydrochloride m.p. 208° C.

In the following Examples 53 to 58 the final reduction step was carried out using the internal reduction method of K. M. Biswas and A. H. Jackson, *Tetrahedron* 24, 1145 (1967).

EXAMPLE 53

1-(5-Phenylfuran-2-ylmethyl)-4-(3-trifluoromethylphenyl)-piperazine 1-(5-Phenyl-2-furoyl)-4-(3-trifluoromethylphenyl)-piperazine (6.0 g, 0.015 mole) and sodium borohydride (1.28 g, 0.034 mole) were stirred in diglyme (25 ml), under nitrogen, and redistilled boron trifluoride etherate (6 ml, 0.045 mole) in diglyme (20 ml) added dropwise with continuous stirring. The resultant clear solution was stirred at room temperature for 3 hours and then evaporated to remove diglyme. The residue was carefully diluted with water (100 ml), followed by 5NHCl (20 ml) and the mixture heated on a steam bath for 15 minutes. The mixture was cooled and made alkaline (4N NaOH) and extracted via diethyl ether. The dried ether extract (MgSO₄) was evaporated to give an oil which failed to crystallise. The product was converted to the hydrochloride and then reconverted to the free base as in Example 40. The base was obtained as a mobile oil which on very strong cooling crystallised, m.p. 56° C.

Similarly prepared were the following:

EXAMPLE 54

1-(5-Phenylfuran-2-ylmethyl)-4-(3,4-dichlorophenyl)-piperazine m.p. 150° C.

EXAMPLE 55

1-(5-Phenylfuran-2-ylmethyl)-4-phenylpiperazine m.p. 106° C.

EXAMPLE 56

1-(5-Phenylfuran-2-ylmethyl)-4-(4-methylphenyl)-piperazine m.p. 114° C.

EXAMPLE 57

1-[5-(3,4-Dimethylphenyl)-furan-2-ylmethyl]-4-(3-trifluoromethyl-4-chlorophenyl)-piperazine m.p. 80° C.

EXAMPLE 58

1-[5-(3,4-Dimethylphenyl)-furan-2-ylmethyl]-4-(3-methoxyphenyl)-piperazine monohydrochloride m.p. 200° C.

EXAMPLE 59

1-[5-(4-methoxyphenyl)-furan-2-ylmethyl]-4-(3-trifluoromethyl-4-chlorophenyl)piperazine m.p. 100° C.

EXAMPLE 60

1-[5-(4-methoxyphenyl)furan-2-ylmethyl]-4-phenylpiperazine m.p. 96° C.

EXAMPLE 61

1-[5-(4-methoxyphenyl)furan-2-ylmethyl]-4-(3-trifluoromethylphenyl)piperazine m.p. 74° C.

EXAMPLE 62

1-(5-Phenylthiophen-2-ylmethyl)-4-phenylpiperazine

5-Phenyl-2-thiophene carboxylic acid (*Khim Geterosikl Soedin,* 1967, 1020 (Russ)) was reacted as in Example 44 to give the title compound (recrystallised from 60/80° C. petroleum ether containing a few drops of ethyl acetate).

m.p. 88° C.

EXAMPLE 63

1-(5-Phenylthiophen-2-ylmethyl)-4-(3-chlorophenyl)piperazine

5-Phenyl-2-thiophenecarboxylic acid was reacted as in Example 44 to the amide which was then reduced to the title compound as in Example 53.

m.p. 115° C.

Similarly prepared were the following:

EXAMPLE 64

1-(5-Phenylthiophen-2-ylmethyl)-4-(4-methoxyphenyl)piperazine m.p. 136° C.

EXAMPLE 65

1-(5-Phenyl-thiophen-2-ylmethyl)-4-(3-trifluoromethyl-4-chlorophenyl)piperazine m.p. 114° C.

EXAMPLE 66

1-(5-Phenylthiophen-2-ylmethyl)-4-(4-methylphenyl)piperazine m.p. 135° C.

EXAMPLE 67

1-(5-Phenylthiophen-2-ylmethyl)-4-(3-trifluoromethylphenyl)piperazine m.p. 94° C.

EXAMPLE 68

1-(5-Phenylthiophen-2-ylmethyl)-4-(4-fluorophenyl)piperazine m.p. 128° C.

EXAMPLE 69

1-(5-Phenylthiophen-2-ylmethyl)-4-(3,4-dimethylphenyl)piperazine m.p. 130° C.

EXAMPLE 70

1-[5-(3,4-Dimethylphenyl)-furan-2-ylmethyl]-4-phenylpiperazine 5-(3,4-Dimethylphenyl)-furan-2-carboxaldehyde (4.0g;0.02 mole), prepared by the method of C. S. Davis and G. S. Lougheed *J.Het.Chem.* 4,153, (1967), was added rapidly to a stirred solution of N-phenylpiperazine (3.2g; 0.02 mole) in methanol (30ml) adjusted to pH 7 (using MeOH/HCl). After 30 minutes a solution of sodium cyanoborohydride (0.48g; 0.0075 mole) in methanol (10ml) was added dropwise and the mixture stirred at room temperature for 2 hours. After removal of the methanol by evaporation, the resultant solid was purified by silica gel chromatography. The fractions containing the desired compound were combined, evaporated and the crystalline solid which formed was recrystallised from 60/80° C. petroleum ether to give the title compound, m.p. 110° C.

Similarly prepared were the following:

EXAMPLE 71

1-[5-(3-trifluoromethyl-4-chlorophenyl)-furan-2-ylmethyl]-4-(4-fluorophenyl)piperazine m.p. 94° C.

EXAMPLE 72

1-[5-(4-Chlorophenyl)-furan-2-ylmethyl]-4-(4-nitrophenyl)piperazine m.p. 149° C.

EXAMPLE 73

1-[5-(4-Methoxyphenyl)furan-2-ylmethyl]-4-(4-methylphenyl)piperazine m.p. 138° C.

EXAMPLE 74

1-[5-(3,4-Dichlorophenyl)furan-2-ylmethyl]-4-(3-trifluoromethylphenyl)piperazine monohydrochloride m.p. 210° C.

EXAMPLE 75

1-(5-Phenylthiophen-2-ylmethyl)-4-(3,4-dichlorophenyl)piperazine m.p. 140° C.

EXAMPLE 76

1-(5-Methylfuran-2-ylmethyl)-4-(3-chlorophenyl)piperazine

5-Methyl-2-furoic acid prepared by the method of D. J. Chadwick et.al. *J. C. S. Perkin I,* 1766 (1973) was reacted as in Example 44 to give the title compound.

b.p. 145° C./0.01 mm (Kugelrohr)

EXAMPLE 77

1-(5-Methylfuran-2-ylmethyl)-4-phenylpiperazine

5-Methyl-2-furoic acid was converted as in Example 44 to the amide which was reduced to the title compound as in Example 53.

b.p. 115° C./0.01mm (Kugelrohr)

Similarly prepared were the following:

EXAMPLE 78

1-(5-Methylfuran-2-ylmethyl)-4-(4-methylphenyl)piperazine m.p. 52° C.

EXAMPLE 79

1-(5-Methylfuran-2-ylmethyl)-4-(4-methoxyphenyl)piperazine m.p. 86° C.

EXAMPLE 80

1-(5-Methylfuran-2-ylmethyl)-4-(4-chlorophenyl)piperazine m.p. 78° C.

EXAMPLE 81

1-(5-Methylfuran-2-ylmethyl)-4-(3-trifluoromethyl-4-chlorophenyl)piperazine

Pale yellow oil, which partially decomposed on distillation.

EXAMPLE 82

1-(5-Methylfuran-2-ylmethyl)-4-(3-trifluoromethylphenyl)piperazine b.p. 105° C./0.02mm(Kugelrohr)

EXAMPLE 83(a)

1-(5-Methylfuran-2-yl-methyl)-4-(4-fluorophenyl)piperazine m.p. 50° C.

EXAMPLE 83(b)

1-(5-Methylfuran-2-ylmethyl)-4-(3,4-dimethylphenyl)piperazine m.p. 47° C.

EXAMPLE 84

1-(5-tert.Butylfuran-2ylmethyl)-4-phenyl piperazine 5-tert-Butyl-2-furoic acid, Bull.Soc.Chim.France 1166(1962), was reacted as in Example 77 to give the title compound.

m.p. 48° C.

Similarly prepared were the following:

EXAMPLE 85

1-(5-tert-Butylfuran-2-yl-methyl)-4-(4-methylphenyl)-piperazine m.p. 62° C.

EXAMPLE 86

1-(5-tert.Butylfuran-2-ylmethyl)-4-(3-chlorophenyl)piperazine b.p. 140° C./0.01mm (Kugelrohr)

EXAMPLE 87

1-(5-tert.Butylfuran-2-ylmethyl)-4-(4-methoxyphenyl)piperazine m.p. 70° C.

EXAMPLE 88

1-(5-tert.Butylfuran-2-ylmethyl)-4-(3-trifluoromethyl-4-chlorophenyl)piperazine b.p. 130° C./0.01mm (Kugelrohr)

EXAMPLE 89

1-(5-tert.Butylfuran-2-ylmethyl)-4-(3-trifluoromethylphenyl)piperazine

Pale yellow oil.

EXAMPLE 90

1-(5-tert-Butylfuran-2-ylmethyl)-4-(4-fluorophenyl)piperazine

Pale yellow oil.

EXAMPLE 91

1-(5-tert.Butylfuran-2-ylmethyl)-4-(3,4-dimethylphenyl)piperazine m.p. 70° C.

EXAMPLE 92

1-[3-(5-Phenylfuran-2-yl)prop-1-yl]-4-phenylpiperazine

5-Phenyl-2-furanpropionic acid, *J. Heterocyc. Chem* 6, 713,(1969) was reacted as Example 77 to give the title compound m.p. 95° C.

Similarly prepared were the following:

EXAMPLE 93

1-[3-(5-Phenylfuran-2-yl)prop-1-yl]-4-(4-methylphenyl)piperazine m.p. 92° C.

EXAMPLE 94

1-[3-(5-Phenylfuran-2-yl)prop-1-yl]-4-(3-trifluoromethylphenyl)piperazine m.p. 56° C.

EXAMPLE 95

1-[3-{5-(4-Chlorophenyl)furan-2-yl}prop-1-yl]-4-(4-methylphenyl)piperazine m.p. 130° C.

EXAMPLE 96

1-[3-{5-(3,4-Dichlorophenyl)furan-2-yl}prop-1-yl]-4-(4-methylphenyl)piperazine m.p. 100° C.

EXAMPLE 97

1-[3-(5-Phenylthiophen-2-yl)prop-1-yl]-4-(4-methylphenyl)piperazine m.p. 92° C.

EXAMPLE 98

(a) 5-Phenyl-2-(2-hydroxyethyl)thiophene

2-Phenylthiophene(16.0g;0.1 mole) was reacted in a similar manner to Example 40 but using ethylene oxide (10ml; 0.2 mole) instead of paraformaldehyde. The title compound was obtained as a pale yellow crystalline solid, m.p. 74° C.

(b)
1-[2-(5-Phenylthiophen-2-yl)ethyl]-4-phenylpiperazine

The hydroxyethyl compound (6.13g; 0.03 mole) from (a) above was reacted as in Example 40 (b), but using thionyl chloride instead of thionyl bromide. The chloroethyl compound was obtained as a straw coloured oil (6.2g) which crystallised on standing, m.p. 40° C. This product was stirred in dioxane (50ml) with N-phenylpiperazine (4.8g;0.03 mole) in the presence of anhydrous sodium carbonate (3.0g) and the mixture heated under reflux for 24 hours. The mixture was filtered from sodium carbonate and the filtrate evaporated to give a pale yellow oil which was taken up in hot 40/60° C. petroleum ether and percolated through a column of silica gel using benzene/ethyl acetate 4:1v/v as developing solvent. The initial fast moving band contained unreacted chloroethyl compound (3.5g). The slower moving band contained the title compound which after recrystallisation from ethyl acetate had m.p. 124° C.

Similarly prepared was:

EXAMPLE 99

1-[2-(5-Phenylthiophen-2-yl)ethyl]-4-(4-methylphenyl)-piperazine m.p. 158° C.

EXAMPLE 100

(a)
1-(5-Phenylfuran-2-ylmethyl)-4-(4-nitrophenyl)piperazine

5-Phenyl-2-furancarboxylic acid was reacted as in Example 44 to the amide which was reduced to the title compound as in Example 53.

m.p. 170° C.

(b)
1-(5-Phenylfuran-2ylmethyl)-4-(4-aminophenyl)piperazine

The product from (a) was hydrogenated and worked up as in Example 36.

m.p. 102° C.

(c)
1-(5-Phenylfuran-2-ylmethyl)-4-(4-methanesulphonamido-phenyl)piperazine

The product from (b) (2.9g;0.009 mole) was stirred in anhydrous ether (50ml) at room temperature and reacted with methanesulphonyl chloride (0.68ml) in the presence of triethylamine (1.2ml). The mixture was stirred overnight, then the ether was evaporated to give a solid which was partitioned between water/chloroform. The chloroform extract was washed with saturated sodium chloride solution and evaporated to give the desired compound as a highly crystalline solid which was recrystallised from ethyl acetate, m.p. 178° C.

Similarly prepared was:

EXAMPLE 101

1-(5-Phenylthiophen-2-ylmethyl)-4-(4-methanesulphonamidophenyl)piperazine m.p. 188° C.

EXAMPLE 102

(a) 5-Phenyl-2-(2-hydroxypropyl)furan

2-Phenylfuran(14.4g,0.1 mole) was reacted in a similar manner to Example 40 but using propylene oxide (9ml,0.13 mole). The title compound was obtained as a straw coloured oil (16.0g) b.p. 145° C./0.05 mm with decomposition.

(b)
1-[2-(5-Phenylfuran-2-yl)prop-1-yl]-4-phenylpiperazine monohydrochloride

The hydroxypropyl compound (8.0g; 0.04 mole) was oxidised to the corresponding ketone by the method of S. L. Huang et al J.O.C. 41, 3329 (1976). The ketone was obtained as a brown oil (4.0g) which was reacted with N-phenylpiperazine and sodium cyanoborohydride as in Example 70, but for 3 days. After purification by column chromatography the title compound was obtained as a straw coloured oil which failed to crystallise and was converted to its monohydrochloride (ethyl acetate-hydrogen chloride) (1.3g) m.p. 206° C.

Similarly prepared were the following:

EXAMPLE 103

1-[2-(5-Phenylthiophen-2-yl)prop-1-yl]-4-phenylpiperazine m.p. 98° C.

EXAMPLE 104

1-[2-(5-Phenylthiophen-2-yl)but-1-yl]-4-phenylpiperazine monohydrochloride m.p. 200° C.

EXAMPLE 105

1-(2-Methylthiazol-4-ylmethyl)-4-(3-bromophenyl)piperazine

A mixture of 4-chloromethyl-2-methylthiazole (7.4g; 0.05 mole), 1-(3-bromophenyl)piperazine (12.05g; 0.05 mole) and anhydrous sodium carbonate (10g) was suspended in absolute ethanol (150 ml). The mixture was stirred and boiled under reflux for 8 hours. The solvent was then evaporated to dryness and water added (100 ml). The emulsion thus formed was extracted with dichloromethane, the organic extracts being dried over magnesium sulphate and evaporated to an oil. This was dissolved in hot benzene, treated with decolourising charcoal and filtered. The filtrate was evaporated to give the title compound as an oil which crystallised completely, m.p. 82° C. (ether).

Similarly prepared were the following:

EXAMPLE 106

1-(2-Methylthiazol-4-ylmethyl)-4-(3-trifluoromethylphenyl)piperazine, dihydrochloride m.p. 176°-8° C.

EXAMPLE 107

1-(2-Methylthiazol-4-ylmethyl)-4-(3-chlorophenyl)piperazine m.p. 71°-2° C.

EXAMPLE 108

1-(2-Methylthiazol-4-ylmethyl)-4-(3-methoxyphenyl)-piperazine m.p. 71.5°–72.5° C.

EXAMPLE 109

1-(2-Methylthiazol-4-ylmethyl)-4-(4-bromophenyl)piperazine m.p. 114°–115° C.

EXAMPLE 110

1-(2-methylthiazol-4-ylmethyl)-4-(2-bromophenyl)piperazine m.p. 85°–86.5° C.

EXAMPLE 111

1-(2-Methylthiazol-4-ylmethyl)-4-(3,4-dichlorophenyl)-piperazine dihydrochloride m.p. 175°–176° C.

EXAMPLE 112

1-(2-Methylthiazol-4-ylmethyl)-4-(3-nitrophenyl)piperazine hydrochloride m.p. 218°–222° C.

EXAMPLE 113

1-(2-Methylthiazol-4-ylmethyl)-4-(4-methylphenyl)piperazine hydrochloride m.p. 190°–2° C.

EXAMPLE 114

1-(2-Methylthiazol-4-ylmethyl)-4-(3-methylphenyl)piperazine hydrochloride m.p. 158°–160° C.

EXAMPLE 115

1-(2-Methylthiazol-4-ylmethyl)-4-(4-chlorophenyl)piperazine m.p. 98° C.

EXAMPLE 116

1-(2-Methylthiazol-4-ylmethyl)-4-(4-chloro-3-trifluoromethylphenyl)piperazine hydrochloride m.p. 185°–7° C.

EXAMPLE 117

1-(2-Methylthiazol-4-ylmethyl)-4-(4-methoxyphenyl)-piperazine hydrochloride m.p. 134°–5° C.

EXAMPLE 118

(a) 2-n-Propyl-4-chloromethylthiazole

To a solution of thiabutanamide (30.96g, 0.3 mole) in absolute ethanol (200ml) was slowly added a solution of 1,3-dichloroacetone (38.1g; 0.3 mole) in ethanol (100ml). The mixture was boiled under reflux for 1 hour and the solvent evaporated. The residue was treated with excess saturated sodium bicarbonate solution and extracted with ether. The extracts were dried and evaporated to a brown oil which was distilled in vacuo to give a pale yellow oil, b.p. 50° C./0.06mm Hg. This was converted to the title compound (hydrochloride salt) using ethereal hydrogen chloride m.p. 60° C. dec.

Similarly prepared were:

(b) 2-Benzyl-4-chloromethylthiazole b.p. 116°–118° C./0.09mm Hg.

(c) 2-isoPropyl-4-chloromethylthiazole hydrochloride m.p. 58° C. (dec.)

EXAMPLE 119

1-(2-n-Propylthiazol-4-ylmethyl)-4-phenylpiperazine

A mixture of 2-n-propyl-4-chloromethylthiazole hydrochloride (3.18g; 0.015 mole), 1-phenylpiperazine (2.43g; 0.015 mole) and sodium carbonate (anhydrous, 10g) in absolute ethanol (60ml) was stirred and boiled under reflux for 6 hours. The suspension was filtered and the filtrate evaporated to a yellow oil. This was dissolved in boiling benzene and treated with decolourising charcoal. After filtration, the benzene was removed giving a yellow oil which crystallised 4.27g. This solid was recrystallised from petroleum ether (b.p. 60°–80° C.) at 0° C. to give a white crystalline solid (m.p. 38°–39° C.)

Similarly prepared were:

EXAMPLE 120

1-(2-n-Propylthiazol-4-ylmethyl)-4-(4-chlorophenyl)-piperazine m.p. 51°–54° C.

EXAMPLE 121

1-(2-n-Propylthiazol-4-ylmethyl)-4-(4-methylphenyl)-piperazine m.p. 41°–44° C.

EXAMPLE 122

1-(2-n-Propylthiazol-4-ylmethyl)-4-(4-methoxyphenyl)-piperazine m.p. 46°–47° C.

EXAMPLE 123

1-(2-n-Propylthiazol-4-ylmethyl)-4-(3-trifluoromethylphenyl)piperazine hydrochloride m.p. 162°–6° C.

EXAMPLE 124

1-(2-n-Propylthiazol-4-ylmethyl)-4-(3,4-dichlorophenyl)piperazine dihydrochloride m.p. 158°–160° C.

EXAMPLE 125

1-(2-n-Propylthiazol-4-ylmethyl)-4-(4-chloro-3-trifluoromethylphenyl)piperazine dihydrochloride m.p. 174°–8° C.

EXAMPLE 126

1-(2-Benzylthiazol-4-ylmethyl)-4-phenylpiperazine m.p. 60°–62° C.

EXAMPLE 127

1-(2-Benzylthiazol-4-ylmethyl)-4-(4-chlorophenyl)piperazine m.p. 74° C.

EXAMPLE 128

1-(2-Benzylthiazol-4-ylmethyl)-4-(4-methoxyphenyl)-piperazine m.p. 65° C.

EXAMPLE 129

1-(2-Benzylthiazol-4-ylmethyl)-4-(3-bromophenyl)piperazine m.p. 69° C.

EXAMPLE 130

1-(2-Benzylthiazol-4-ylmethyl)-4-(4-chloro-3-trifluoromethylphenyl)piperazine

Colourless oil.

EXAMPLE 131

1-[2-(4-chlorobenzyl)-thiazol-4-ylmethyl]-4-phenyl piperazine dihydrochloride m.p. 150° C. (Dec.)

EXAMPLE 132

1-(2-isoPropylthiazol-4-ylmethyl)-4-(4-chlorophenyl)-piperazine m.p. 54° C.

EXAMPLE 133

1-(2-isoPropylthiazol-4-ylmethyl)-4-phenylpiperazine m.p. 42° C.

EXAMPLE 134

1-(2-isoPropylthiazol-4-ylmethyl)-4-(3-methoxyphenyl)piperazine m.p. 65° C.

EXAMPLE 135

1-(2-isoPropylthiazol-4-ylmethyl)-4-(3-bromophenyl)-piperazine

Colourless oil.

EXAMPLE 136

1-(2-isoPropylthiazol-4-ylmethyl)-4-(4-chloro-3-trifluoromethylphenyl piperazine Colourless oil.

The following further Examples illustrate the preparation of pharmaceutical formulations containing compounds of the invention. The active compound utilised was 1-(2-benzylthiazol-4-ylmethyl)-4-phenylpiperazine, although it will be appreciated by those skilled in the art that other active solid compounds of the invention could equally well be used.

EXAMPLE 137

Hard gelatin capsules were prepared using the following ingredients:

|  | Quantity (mg/capsule) |
| --- | --- |
| Active compound | 250 |
| Starch dried | 200 |
| Magnesium stearate | 10 |

The above ingredients were mixed and filled into hard gelatin capsules.

EXAMPLE 138

The above procedure was repeated except that microcrystalline cellulose was used in place of starch.

EXAMPLE 139

Tablets were prepared using the following components:

|  | Quantity (mg/tablet) |
| --- | --- |
| Active compound | 500 |
| Starch | 100 |
| Magnesium stearate | 7 |
| Amberlite XE88 | 5 |

The starch and active compound were mixed together and sufficient water added for a uniform dispersion to be attained. The mixture was then wet screened and dried. After drying the material was screened again, and the magnesium stearate and amberlite resin then added. Finally the mixture was compressed into tablets.

EXAMPLE 140

An alternative tablet formula was prepared using the ingredients below:

|  | Quantity (mg/tablet) |
| --- | --- |
| Active compound | 250 |
| Cellulose microcrystalline | 400 |
| Silicon dioxide fumed | 10 |
| Stearic acid | 5 |

The components were blended and compressed to form tablets.

EXAMPLE 141

An aerosol solution was prepared containing the following components:

|  | Weight % |
| --- | --- |
| Active ingredient | 0.25 |
| Ethanol | 29.75 |
| Propellant 22 (Chlorodifluoromethane) | 70 |

The active compound was mixed with ethanol and the mixture added to the propellant 22, cooled to −30° C. and transferred to a filling device. The required amount was then fed to a stainless steel container and diluted further with a metered amount of propellant. The valve units were then fitted to the container.

EXAMPLE 142

A suppository formula was prepared containing 200mg of the compound using the following ingredients:

| Active compound | 200mg |
| --- | --- |
| Polyethylene glycol 1000 | 750mg |
| Polyethylene glycol 4000 | 250mg |

The active compound was mixed in the molten glycol bases and then the mixture was poured into appropriate suppository moulds, to give the active fill weight.

EXAMPLE 143

An ointment was made to the following formula:

| Active compound | 1% by weight |
|---|---|
| White soft paraffin | q.s. to 100% |

The active compound was added to the molten paraffin and then the mixture was allowed to cool.

EXAMPLE 144

A topical cream was prepared having the following ingredients:

| | grams |
|---|---|
| Active compound | 0.5 |
| Cetomacrogol 1000 | 2.8 |
| Cetostearyl alcohol | 11.2 |
| Liquid paraffin | 8.0 |
| Water | q.s. to 100 |

The active principle was suspended in liquid paraffin. The cetostearyl alcohol was added and the mixture heated to 70° C. with stirring. The cetomacrogol 1000 was dissolved in 60g. of water and heated to 70° C. The two solutions were then mixed with stirring, and stirring continued until the temperature fell to ambient. The cream was then made up to weight with water and passed through a stainless steel colloid mill set at a gap of 15/1000 inch.

We claim:

1. A phenylpiperazine derivative which is a furan of formula (II):

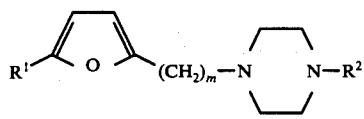

(II)

where $R^1$ is phenyl or phenyl substituted by one or two radicals selected from halogen, $C_{1-4}$ alkyl, $C_{1-4}$ alkoxy and $C_{1-4}$ haloalkyl; $R^2$ is phenyl or phenyl substituted by $C_{1-4}$ alkyl, amino, $C_{1-4}$ alkylsulphonamido and $C_{1-4}$ alkoxy and $m$ is 1 or 3, with the exception of compounds in which $R^1$ is unsubstituted phenyl, $m$ is 1 and $R^2$ is unsubstituted phenyl; or where $R^1$ is methyl, $m$ is 1 and $R^2$ is phenyl or phenyl substituted by a single radical selected from halogen, $C_{1-4}$ alkyl, $C_{1-4}$ alkoxy, $C_{1-4}$ haloalkyl or is disubstituted by two $C_{1-4}$ alkyl radicals; or a pharmaceutically-acceptable salt thereof.

2. A phenylpiperazine which is a thiophene of formula (III):

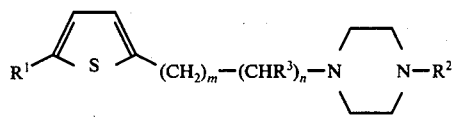

(III)

where $R^1$ is phenyl; $R^2$ is phenyl, phenyl singly substituted by $C_{1-4}$ alkyl or $C_{1-4}$ haloalkyl or doubly substituted by two radicals selected from the group comprising halogen, $C_{1-4}$ haloalkyl and $C_{1-4}$ alkyl, and where $m$ is 1 or 2 and $n = 0$; or where $m$ is 1, $n$ is 1 and $R^3$ is ethyl; or a pharmaceutically-acceptable salt thereof.

3. A phenylpiperazine which is an oxazole of formula (IV):

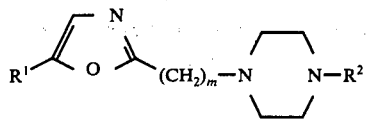

(IV)

where $R^1$ is phenyl optionally substituted by $C_{1-4}$ alkoxy or halogen; $R^2$ is phenyl optionally substituted by $C_{1-4}$ alkyl, $C_{1-4}$ haloalkyl, halogen, amino or $C_{2-4}$ alkanoylamino and $m$ is 1 or 2; or a pharmaceutically-acceptable salt thereof.

4. A phenylpiperazine of formula (I) according to claim 1, which is a thiazole of formula:

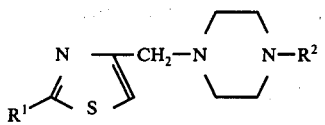

where $R^1$ is benzyl, $R^2$ is phenyl or p-halophenyl; or a pharmaceutically-acceptable salt thereof.

5. A phenylpiperazine of formula (I) according to claim 1 which is a thiazole of formula:

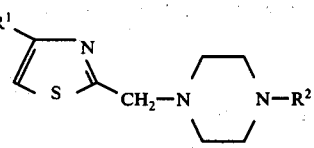

where $R^1$ is $C_{1-4}$ alkyl, phenyl or phenyl substituted by $C_{1-4}$ alkyl, $C_{1-4}$ alkoxy, nitro and $C_{1-4}$ haloalkyl and $R^2$ is phenyl or phenyl substituted by $C_{1-4}$ haloalkyl; or a pharmaceutically-acceptable salt thereof.

6. A compound according to claim 2 which is 1-[2-(5-phenylthiophen-2-yl)ethyl]-4-phenylpiperazine.

7. A compound according to claim 1 which is 1-(5-methylfuran-2-ylmethyl)-4-(3-chlorophenyl)piperazine.

8. A compound according to claim 1 which is 1-[5-(4-methoxyphenyl)-furan-2-ylmethyl]-4-phenylpiperazine.

9. A compound according to claim 1 which is 1-[5-(3,4-dimethylphenyl)-furan-2-ylmethyl]-4-phenylpiperazine.

10. A compound according to claim 1 which is 1-{3-[5-(3,4-dichlorophenyl)-furan-2-yl]prop-1-yl}-4-(4-methylphenyl)piperazine.

11. A compound according to claim 2 which is 1-[2-(5-phenylthiophen-2-yl)but-1-yl]-4-phenylpiperazine.

12. A compound according to claim 2 which is 1-(5-phenylthiophen-2-ylmethyl)-4-(3,4-dimethylphenyl)-piperazine.

13. A compound according to claim 1 which is 1-[3-(5-phenylfuran-2-yl)prop-1-yl]-4-(4-methylphenyl)piperazine.

14. A compound according to claim 1 which is 1-[5-(4-methoxyphenyl)-furan-2-ylmethyl)]-4-(4-methylphenyl)piperazine.

15. A compound according to claim 3 which is 1-(5-phenyloxazol-2-ylmethyl)-4-(4-methylphenyl)-piperazine.

16. A compound according to claim 4 which is 1-(2-benzylthiazol-4-ylmethyl)-4-phenylpiperazine.

17. A pharmaceutical formulation which comprises an effective amount of a compound of formula (I) as claimed in claim 4, or a pharmaceutically-acceptable table salt thereof, associated with a pharmaceutically-acceptable carrier therefor.

18. A method of treating a mammal, including a human, suffering from, or susceptible to, an immediate hypersensitivity condition such as asthma which comprises administering to the mammal a chemotherapeutically effective amount of a compound of formula (I) as claimed in claim 4.

* * * * *

UNITED STATES PATENT AND TRADEMARK OFFICE
CERTIFICATE OF CORRECTION

PATENT NO. : 4,123,529

DATED : October 31, 1978

INVENTOR(S) : John P. Verge et al.

It is certified that error appears in the above-identified patent and that said Letters Patent are hereby corrected as shown below:

Column 9, line 19, "consists" should read -- consist --.

Column 11, line 41, "60°-80°0 C." should read -- 60°-80°C. --.

Column 12, line 58, "as added slowly" should read -- was added slowly --.

Column 12, line 68, "several time" should read -- several times --.

Column 28, lines 7-8, should read --where $R^1$ is phenyl or phenyl substituted by $C_{1-4}$ alkoxy or halogen; $R^2$ is phenyl or phenyl substituted by $C_{1-4}$ --.

Column 28, lines 12-13, should read -- 4. A phenylpiperazine which is a thiazole of formula: --.

Column 28, lines 22-23, should read -- 5. A phenylpiperazine which is a thiazole of formula: --.

Column 28, lines 59-60, should read -- 17. A pharmaceutical formulation which contains an effective amount of a compound as --.

Signed and Sealed this

Twenty-fifth Day of September 1979

[SEAL]

Attest:

LUTRELLE F. PARKER

Attesting Officer   Acting Commissioner of Patents and Trademarks